United States Patent
Jugl et al.

(10) Patent No.: US 10,232,122 B2
(45) Date of Patent: Mar. 19, 2019

(54) DRIVE MECHANISM FOR DRUG DELIVERY DEVICE

(75) Inventors: Michael Jugl, Frankfurt am Main (DE); Gunther Sendatzki, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 198 days.

(21) Appl. No.: 13/392,772

(22) PCT Filed: Sep. 3, 2010

(86) PCT No.: PCT/EP2010/062931
§ 371 (c)(1),
(2), (4) Date: Jul. 19, 2012

(87) PCT Pub. No.: WO2011/026931
PCT Pub. Date: Mar. 10, 2011

(65) Prior Publication Data
US 2012/0283661 A1    Nov. 8, 2012

(30) Foreign Application Priority Data
Sep. 7, 2009 (EP) .................................... 09011418

(51) Int. Cl.
*A61M 5/315* (2006.01)
*A61M 5/24* (2006.01)
*A61M 5/31* (2006.01)

(52) U.S. Cl.
CPC .... *A61M 5/31561* (2013.01); *A61M 5/31551* (2013.01); *A61M 5/31583* (2013.01);
(Continued)

(58) Field of Classification Search
CPC ........ A61M 5/20; A61M 5/315; A61M 5/286; A61M 5/2429; A61M 5/2425;
(Continued)

(56) References Cited

U.S. PATENT DOCUMENTS

| 533,575 A | 2/1895 | Wilkens |
| 3,790,048 A * | 2/1974 | Luciano ............ A61M 5/31553 222/390 |

(Continued)

FOREIGN PATENT DOCUMENTS

| EP | 0937471 A2 | 8/1999 |
| EP | 0937476 A2 | 8/1999 |

(Continued)

OTHER PUBLICATIONS

Form PCT/IPEA/409, International Preliminary Report on Patentability.

*Primary Examiner* — Bradley J Osinski
*Assistant Examiner* — Matthew A Engel
(74) *Attorney, Agent, or Firm* — Fish & Richardson, P.C.

(57) ABSTRACT

A drive mechanism for a drug delivery device, preferably for a pen-type injector, the mechanism comprises a spindle (6) movable in a first direction during a delivery step, a splined portion (5, 11) operatively coupled to the spindle (6), and retraction means (12, 15, 16, 17, 20) acting on the splined portion (5, 11) at least at the end of the delivery step. Thereby, that after the delivery step the spindle (6) and/or the splined portion (5, 11) is moved in a second direction contrary to the first direction, such that the whole drive mechanism is relieved from stresses.

14 Claims, 9 Drawing Sheets

(52) U.S. Cl.
CPC ........... *A61M 5/24* (2013.01); *A61M 5/31593* (2013.01); *A61M 2005/2407* (2013.01); *A61M 2005/3103* (2013.01); *A61M 2005/3112* (2013.01)

(58) Field of Classification Search
CPC .............. A61M 5/282; A61M 5/31586; A61M 2005/2414; A61M 5/3272; A61M 5/3293; A61M 5/2466
USPC .......................... 604/200, 208–211, 224, 192
See application file for complete search history.

(56) References Cited

U.S. PATENT DOCUMENTS

| | | | |
|---|---|---|---|
| 4,266,541 A * | 5/1981 | Landau | A61M 5/30 604/68 |
| 4,581,022 A * | 4/1986 | Leonard | A61M 5/31581 222/391 |
| 4,659,327 A | 4/1987 | Bennett et al. | |
| 4,710,178 A * | 12/1987 | Henri | A61M 5/31581 401/181 |
| 4,865,591 A * | 9/1989 | Sams | A61M 5/31553 222/287 |
| 4,973,318 A * | 11/1990 | Holm | A61M 5/24 604/208 |
| 5,112,317 A * | 5/1992 | Michel | A61M 5/24 222/386 |
| 5,226,895 A | 7/1993 | Harris | |
| 5,279,585 A * | 1/1994 | Balkwill | A61M 5/3158 222/309 |
| 5,279,586 A | 1/1994 | Balkwill | |
| 5,304,152 A | 4/1994 | Sams | |
| 5,320,609 A | 6/1994 | Haber et al. | |
| 5,380,295 A | 1/1995 | Vacca | |
| 5,383,865 A | 1/1995 | Michel | |
| 5,480,387 A | 1/1996 | Gabriel et al. | |
| 5,505,704 A | 4/1996 | Pawelka et al. | |
| 5,545,147 A * | 8/1996 | Harris | A61M 5/31551 604/208 |
| 5,569,190 A * | 10/1996 | D'Antonio | A61M 5/2425 604/135 |
| 5,582,598 A | 12/1996 | Chanoch | |
| 5,591,138 A * | 1/1997 | Vaillancourt | A61M 5/3271 604/192 |
| 5,626,566 A | 5/1997 | Petersen et al. | |
| 5,643,214 A * | 7/1997 | Marshall | A61M 5/2033 604/131 |
| 5,674,204 A | 10/1997 | Chanoch | |
| 5,688,251 A | 11/1997 | Chanoch | |
| 5,713,857 A * | 2/1998 | Grimard | A61M 5/31596 604/218 |
| 5,851,197 A * | 12/1998 | Marano | A61M 5/158 604/131 |
| 5,921,966 A | 7/1999 | Bendek et al. | |
| 5,957,897 A * | 9/1999 | Jeffrey | 604/223 |
| 5,961,495 A | 10/1999 | Walters et al. | |
| 6,004,297 A | 12/1999 | Steenfeldt-Jensen et al. | |
| 6,068,614 A * | 5/2000 | Kimber | A61M 5/178 264/478 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,599,272 B1 * | 7/2003 | Hjertman | A61M 5/315 604/197 |
| 6,899,698 B2 | 5/2005 | Sams | |
| 6,936,032 B1 | 8/2005 | Bush, Jr. et al. | |
| 7,094,221 B2 * | 8/2006 | Veasey | A61M 5/31551 604/187 |
| 7,195,616 B2 * | 3/2007 | Diller | A61M 5/31566 604/207 |
| 7,241,278 B2 * | 7/2007 | Moller | A61M 5/24 604/211 |
| 7,297,136 B2 * | 11/2007 | Wyrick | 604/117 |
| 7,427,275 B2 * | 9/2008 | DeRuntz | A61M 5/31551 604/187 |
| 7,481,977 B2 * | 1/2009 | Percival | B01L 3/5025 210/324 |
| 7,850,662 B2 * | 12/2010 | Veasey | A61M 5/31546 604/207 |
| 7,918,833 B2 * | 4/2011 | Veasey | A61M 5/31546 604/209 |
| 7,935,088 B2 * | 5/2011 | Veasey | A61M 5/31546 604/207 |
| 7,985,201 B2 * | 7/2011 | Langley | A61M 5/20 604/131 |
| 7,993,301 B2 * | 8/2011 | Boyd | A61M 5/31555 604/211 |
| 8,257,319 B2 * | 9/2012 | Plumptre | A61M 5/31525 604/211 |
| 9,108,031 B2 * | 8/2015 | Brandenburger | A61J 1/2096 |
| 2002/0052578 A1 | 5/2002 | Moller | |
| 2002/0120235 A1 | 8/2002 | Enggaard | |
| 2003/0050609 A1 | 3/2003 | Sams | |
| 2003/0105430 A1 * | 6/2003 | Lavi | A61M 5/2033 604/136 |
| 2004/0059299 A1 | 3/2004 | Moller | |
| 2004/0153003 A1 * | 8/2004 | Cicenas | A61B 10/0275 600/564 |
| 2004/0210199 A1 * | 10/2004 | Atterbury | A61M 5/31566 604/224 |
| 2004/0249348 A1 * | 12/2004 | Wimpenny | A61M 5/3158 604/207 |
| 2004/0260247 A1 * | 12/2004 | Veasey | A61M 5/31551 604/207 |
| 2004/0267207 A1 | 12/2004 | Veasey et al. | |
| 2005/0033244 A1 * | 2/2005 | Veasey | A61M 5/31546 604/211 |
| 2005/0113765 A1 | 5/2005 | Veasey et al. | |
| 2005/0154353 A1 | 7/2005 | Alheidt | |
| 2005/0182371 A1 | 8/2005 | Wagner et al. | |
| 2006/0153693 A1 | 7/2006 | Fiechter et al. | |
| 2006/0264839 A1 * | 11/2006 | Veasey | A61M 5/31546 604/209 |
| 2008/0027397 A1 * | 1/2008 | DeRuntz | A61M 5/31551 604/220 |
| 2008/0262436 A1 * | 10/2008 | Olson | A61M 5/2033 604/198 |
| 2009/0198193 A1 * | 8/2009 | Veasey | A61M 5/31546 604/207 |
| 2009/0264828 A1 * | 10/2009 | Dette | A61M 5/31533 604/189 |
| 2009/0275916 A1 | 11/2009 | Harms et al. | |
| 2010/0094205 A1 * | 4/2010 | Boyd | A61M 5/31595 604/68 |
| 2010/0094206 A1 * | 4/2010 | Boyd | A61M 5/31555 604/68 |
| 2010/0094207 A1 * | 4/2010 | Boyd | A61M 5/31555 604/68 |
| 2010/0094253 A1 * | 4/2010 | Boyd | A61M 5/31555 604/506 |
| 2010/0137792 A1 * | 6/2010 | Boyd | A61M 5/31555 604/68 |
| 2010/0324494 A1 * | 12/2010 | Plumptre | A61M 5/31551 604/207 |
| 2010/0324496 A1 * | 12/2010 | Plumptre | A61M 5/24 604/207 |
| 2010/0324497 A1 * | 12/2010 | Plumptre | A61M 5/24 604/207 |
| 2010/0324527 A1 * | 12/2010 | Plumptre | A61M 5/31536 604/500 |
| 2010/0331788 A1 * | 12/2010 | Plumptre | A61M 5/31543 604/207 |
| 2010/0331790 A1 * | 12/2010 | Plumptre | A61M 5/31511 604/207 |
| 2010/0331791 A1 * | 12/2010 | Plumptre | A61M 5/31551 604/207 |
| 2010/0331792 A1 * | 12/2010 | Plumptre | A61M 5/31525 604/207 |

(56) References Cited

U.S. PATENT DOCUMENTS

| | | | |
|---|---|---|---|
| 2010/0331806 A1* | 12/2010 | Plumptre | A61M 5/31543 604/500 |
| 2011/0152784 A1* | 6/2011 | Veasey | A61M 5/31546 604/207 |
| 2012/0010575 A1* | 1/2012 | Jones | A61M 5/31555 604/211 |
| 2012/0022462 A1* | 1/2012 | Plumptre | A61M 5/3129 604/197 |
| 2012/0046643 A1* | 2/2012 | Plumptre | A61M 5/31551 604/506 |
| 2012/0089098 A1* | 4/2012 | Boyd | A61M 5/24 604/189 |
| 2012/0089100 A1* | 4/2012 | Veasey | A61M 5/31546 604/209 |
| 2012/0283649 A1* | 11/2012 | Veasey | A61M 5/31535 604/208 |
| 2012/0283651 A1* | 11/2012 | Veasey | A61M 5/31543 604/210 |
| 2012/0283652 A1* | 11/2012 | MacDonald | A61M 5/24 604/211 |
| 2012/0283653 A1* | 11/2012 | MacDonald | A61M 5/24 604/211 |
| 2012/0283654 A1* | 11/2012 | MacDonald | A61M 5/24 604/211 |
| 2012/0283658 A1* | 11/2012 | Plumptre | A61M 5/24 604/211 |
| 2012/0283661 A1* | 11/2012 | Jugl | A61M 5/31551 604/224 |
| 2012/0283662 A1* | 11/2012 | MacDonald | A61M 5/24 604/236 |
| 2013/0030409 A1* | 1/2013 | Macdonald | A61M 5/24 604/506 |
| 2014/0316347 A1* | 10/2014 | Veasey | A61M 5/31546 604/211 |

FOREIGN PATENT DOCUMENTS

| | | |
|---|---|---|
| EP | 1603611 B1 | 12/2005 |
| EP | 1666081 | 6/2006 |
| EP | 1666081 A2 | 6/2006 |
| EP | 2016962 | 1/2009 |
| EP | 2016962 A1 | 1/2009 |
| WO | 9426331 A1 | 11/1994 |
| WO | WO 94/26331 | 11/1994 |
| WO | 9938554 A1 | 8/1999 |
| WO | 0110484 A1 | 2/2001 |

* cited by examiner

DRIVE MECHANISM FOR DRUG DELIVERY DEVICE

CROSS REFERENCE TO RELATED APPLICATIONS

The present application is a 35 U.S.C. 371 National Application of PCT/EP2010/062931 filed Sep. 3, 2010, which claims priority to European Patent Application No. 09011418.2, filed Sep. 7, 2009, the entire contents of which are incorporated entirely herein by reference.

The present invention concerns a drive mechanism for a drug delivery device, in particular for pen-type injectors of the kind that provide for administration by injection of medicinal products, i.e. drugs to be delivered, from a drug containing cartridge, preferably where a user may set the dose on its own.

Drug delivery devices are applied where regular injection by persons without formal medical training occurs. This is increasingly common amongst, for instance, those having diabetes, where self-treatment enables such persons to conduct effective management of their disease.

These circumstances require some provisions for drug delivery devices of such kind. The devices must be robust in construction, easy to use both in terms of the manipulation of the parts and understanding by a user of its operation. In the case of those with diabetes, many users will be physically infirm and may also have impaired vision.

EP 1 603 611 B1 discloses a drive mechanism of the generic kind for use in a drug delivery device. This device comprises a housing, a dose dial means engaging with the housing, a splined portion releasably connected to the dose dial means and a clutch means located between the dose dial means and the splined portion. In a first mode, when the dose dial means and the splined portion are coupled, both are allowed to rotate with respect to the housing. In contrast in a second mode, when the dose dial means and the splined portion are de-coupled, rotation of the dose dial means with respect to the housing is allowed, whilst rotation of the splined portion with respect to the housing is not allowed, whereby axial movement of the splined portion is transferred to a spindle to move said spindle in the longitudinal direction towards the proximal end of the drug delivery device.

During the operation of such conventional drive mechanisms for drug delivery devices, an axial force is exerted to a plug within a drug containing cartridge is loaded with force by a spindle via a disk in order to dispense drugs to be delivered at the proximal end. Due to the load with force the plug is deformed, i.e. compressed while dispensing the drugs. After having ended the operation, the deformation of the plug imposes forces to the whole system including the drive mechanism and the delivery system of the spindle.

On the one hand, the remaining forces lead to dropping of the drugs to be delivered in the standby position of the delivery system and to an increase in dwell time, since the plug can only relax in the direction of the drug containing cartridge. On the other hand, the compressed plug imposes a stress to the spindle and the splined portion, which makes the handling uncomfortable.

It is the object of the present invention, to overcome the drawbacks of the state of the art by providing an enhanced drive mechanism.

This object is solved by a drive mechanism according to claim 1.

In particular, the object of the invention is achieved by a drive mechanism for a drug delivery device, preferably for a pen-type injector, said mechanism comprising a spindle movable in a first direction during a delivery step, a splined portion operatively coupled to said spindle, and retraction means acting on said splined portion at least at the end of said delivery step such that after said delivery step said spindle or said spindle together with said splined portion is/are moved in a second direction contrary to said first direction. In other words, the retraction means are designed and arranged to shift the spindle and/or the splined portion in the distal direction of the drive mechanism after a previously selected amount of drug has been administered. This does not only reduce the forces acting on the drive mechanism but also allows the plug to relax thus reducing the dwell time and the risk of dropping of the drug.

Preferably, the retraction means is designed as an elastic portion or a spring element, wherein more preferably the elastic portion is designed as a rubber element cushioning a spline socket engaging with the spindle.

In a preferred embodiment, the drive mechanism further comprises a housing, with the retraction means being arranged between the splined portion and the housing. In another preferred embodiment, the retraction means and the splined portion is an integrally moulded component of the housing.

The drive mechanism of the present invention may further comprise a cartridge holder for accommodating a drug containing cartridge, with the retraction means being arranged between the splined portion and the drug containing cartridge. More preferably, the splined portion is designed as a driver acting on the spindle to move the spindle in the first direction during the delivery step. Further, the splined portion may be designed as a spindle nut rotationally fixed with respect to the housing.

Preferably, the in the above drive mechanism the spindle abuts to a hollow plug having a cup-shape and being of flexible material, wherein the hollow plug acts in a cartridge containing a drug to be delivered. More preferably, this hollow plug has a wall thickness of at least 1 mm, a bottom thickness of at least 1 mm and a clearance between the centreline perpendicular to the axial direction and the inner bottom face of at least 1 mm.

The term "drug delivery device" according to the present invention shall preferably mean a single-dose or multi-dose, disposable or re-usable device designed to dispense a selected dose of a medicinal product, preferably multiple selected doses, e.g. insulin, growth hormones, low molecular weight heparines, and their analogues and/or derivatives etc. In particular, the term "drug delivery device" shall mean a disposable multi-dose pen-type device having mechanical and manual dose delivery and dose selection mechanism, which is designed for regular use by persons without formal medical training such as patients. Preferably, the drug delivery device is of the injector-type.

The term "housing" according to the present invention shall preferably mean any exterior housing such as main housing, body or shell or interior housing such as insert or inner body. The housing may be designed to enable the safe, correct and comfortable handling of the drug delivery device or any of its mechanism. Usually, it is designed to house, fix, protect, guide and/or engage with any of the inner components of the drug delivery device, e.g. the drive mechanism, cartridge, spindle and/or splined portion, by limiting the exposure to contaminants such as liquid, dust, dirt etc. In general, the housing may be an integral or a multipart component of tubular or non-tubular shape. The exterior housing may comprise a cartridge holder to house a cartridge from which a number of doses of a medicinal product may be dispensed.

The term "proximal end" shall preferably mean the end of the device or a component, which is closest to the dispensing end of the device. The term "distal end" shall mean the end of the device or a component, which is furthest away from the dispensing end of the device.

The term "splined portion" shall preferably mean a keyed or slotted portion which engages with a slotted or keyed or complementary portion of the spindle. Preferably, "splined portion" and its engagement should be as such, that axial forces can be transmitted via the engagement between the piston rod and the splined portion. According to a preferred embodiment the spindle is designed as a threaded piston rod and the first splined portion is designed as a nut-like element which is in engagement with the threaded piston rod. Further, the pitch of the two corresponding threads may be chosen such that a small relative movement between the piston rod and the nut is allowed. It is preferred to provide a spindle being a double-threaded piston rod having two outer threads, one of which is in threaded engagement with the first splined portion and the other thread being in threaded engagement with an inner thread of a drive sleeve or the like element. The two threads of the spindle may have a different pitch and/or may be of opposite hand.

In the following, the invention will be described by way of examples and referring to the Figures.

Figure 1:
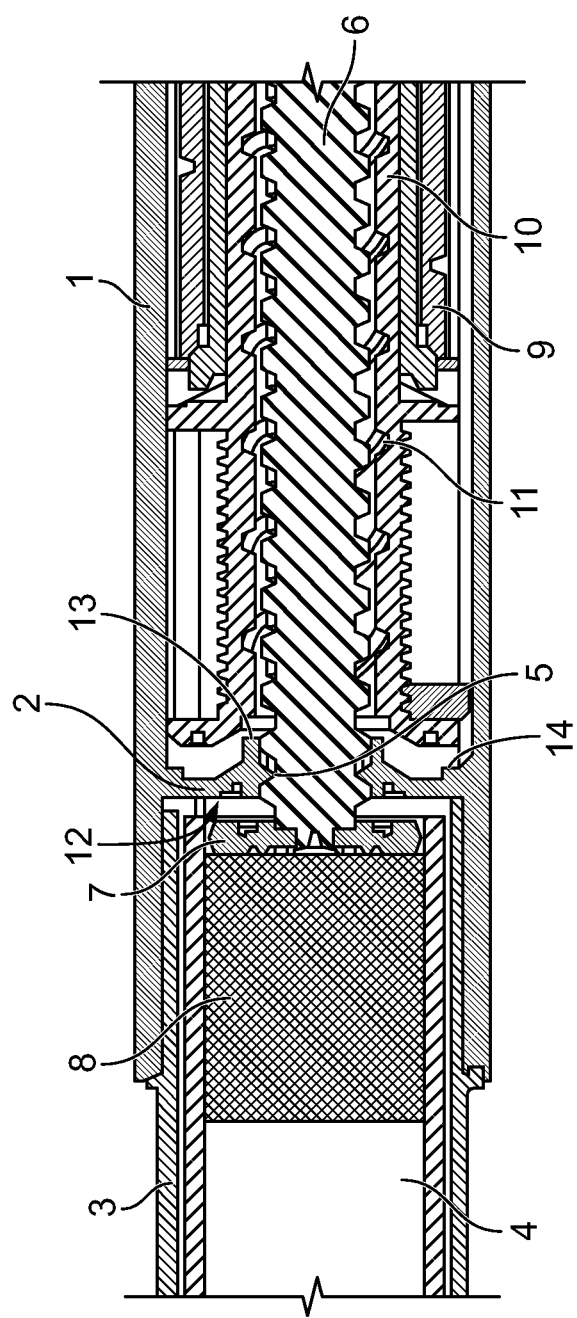
FIG. 1 shows a schematic sectional view of the drive mechanism according to a first embodiment of the invention.

The general assembly of a drug delivery device of the generic kind comprises a housing 1 of substantially circular cross-section having a bottom portion 2 on its proximal end and adjacent thereto a cartridge holder 3 for receiving a drug containing cartridge 4, which is fixed to the proximal end of the housing 1. The bottom portion 2 may comprise a first splined portion 5 or socket engaging with a spindle 6. In the embodiment depicted in FIG. 1, the spindle 6 is a piston rod having a first outer thread which engages a first inner thread defined by the first splined portion 5. In other words, the bottom portion 2 may comprise a nut-like element for threaded engagement with the threaded spindle 6. The threads of the spindle 6 and the e.g. nut-like first splined portion 5 are designed such that there is a small clearance between the splines or grooves defining the threads. This allows a small relative movement between the spindle 6 and the first splined portion 5 in the axial direction of the device. The spindle 6 is provided on its proximal end with a disk 7 abutting against a plug 8 of the drug containing cartridge 4. By the proximal movement of the spindle 6, the plug 8 is forced into the drug containing cartridge 4 thereby dispending the drug to be delivered.

A dose dial sleeve 9 (number sleeve) for presetting the drug dose to be delivered is accommodated in the housing 1 and is releasably connected via a clutch means to a drive sleeve 10 acting within this dose dial sleeve 9. The drive sleeve 10 comprises a second splined portion 11 on its inner wall engaging with the spindle 6. In the embodiment depicted in FIG. 1, the spindle 6 is a piston rod having a second outer thread (not shown) which engages a second inner thread defined by the second splined portion 11 on the inside of the drive sleeve 10.

On the distal end of the drug delivery device, a dose knob is provided on the dose dial sleeve 9. The dose dial sleeve 9 is screwed out of the housing 1 so as to set a predetermined amount of drug to be delivered. To inject (deliver) the drug amount, the dose dial knob may be pushed towards the proximal end of the device, thus pushing the dose dial sleeve and the drive sleeve in the same direction, which causes the spindle 6 to be rotated (screwed) to the proximal direction for suspending the drug to be delivered towards the proximal end of the whole device.

While operating the drive mechanism of the present invention, the first splined portion 5 is operatively coupled to the spindle 6 moving in a first direction. In contrast to the above-mentioned state of the art, at least at the end of the delivery step retraction means 12 act on the first splined portion 5 such that after the delivery step the spindle 6 and/or the first splined portion 5 is/are moved in a second direction contrary to said first direction. Thereby, the first splined portion 5 and the spindle 6 are relaxed and allowed to return in their standby position. This relaxing movement may be just a movement within the clearance of the respective threads of the first splined portion 5 and the spindle 6.

A schematic view of the drive mechanism according to the present invention is given in FIG. 1.

For instance, during the delivery step the spindle 6 moves plug 8 to the proximal end of the drug delivery device, i.e. into a drug containing cartridge 4. At least after the end of the delivery step, i.e. when a user releases the dose knob or the like the retraction means 12 act on the spindle 6 and/or the first splined portion 5 such that they are moved towards the distal end of the drug delivery device, i.e. out of the drug containing cartridge 4.

Thereby, the first splined portion 5 and the spindle 6 are relaxed and allowed to return in their standby position. By its returning, the spindle 6 is retracted from the plug 8 within the drug containing cartridge 4 which in turn is allowed to relax towards the spindle 6 without dispensing further drugs to be delivered. In other words, the retraction means 12 exert a restoring force to the spindle 6 and/or the first splined portion 5. Preferably, the spindle 6 and/or a disc associated to the spindle 6 remain in contact with the distal face of the plug 8 during said step of relaxing or retracting.

The drive mechanism of the present invention provides substantial advantages compared to the state of the art.

By applying the drive mechanism of the present invention (also in either embodiment described hereinafter), the whole drug delivery device is relieved from stresses. The stress-relieved spindle 6 and/or first splined portion 5 contribute to the reduction of the dwell time for users in the standby position and during dialing. The stress-relief of the plug 8 within the drug containing cartridge 4 remarkably reduces the dropping of the drugs to be delivered from the proximal end of the drug delivery device.

Preferably, the drive mechanism according to the present invention is accommodated in a housing 1, with said retraction means 12 being arranged between said first splined portion 5 and said housing 1. As an alternative, the drive mechanism may further comprise a cartridge holder 3 for accommodating a drug containing cartridge 4, with the retraction means 12 being arranged between said first splined portion 5 and said drug containing cartridge 4.

Further preferably, the first splined portion 5 is designed as a driver acting on said spindle to move said spindle 6 in the first direction during the delivery step. In addition, the first splined portion 5 may be designed as a spindle 6 nut rotationally fixed with respect to the housing 1.

First Embodiment

According to a first embodiment, the retraction means 12 and the first splined portion 5 are an integrally moulded component of the housing 1. The housing 1 may have a cylindrical shape with an inner wall or bottom portion 2 extending radially inwards from the inner surface of the housing 1. The radially inner edge of the bottom portion 2 is provided with a first splined portion 5 which is in engagement with the spindle 6. Preferably, a deformable bottom portion 2 of the housing 1, being the retraction means 12 and exhibiting flexibility, comprises the first splined portion 5 integrally moulded therewith. While operating the drive mechanism of the present invention, a drive sleeve 10 operatively coupled to the spindle 6 is moved onto a first dead stop 13 of the bottom portion. When the drive sleeve 10 is further moved beyond this first dead stop 13, at least the radially inner edge of the bottom portion 2 is axially displaced so that the proximal face of the drive sleeve 10 contacts a second dead stop 14 of the bottom portion 2 being the end stop. In other words, the first abutment of the proximal face of the drive sleeve 10 bends the first splined portion 5 in the proximal direction.

After having ended the operation, the axially displaced bottom portion 2 of the housing 1 exerts a restoring force in the opposite direction of the movement of the first splined portion 5. Thereby, the drive sleeve 10 and the spindle 6 (which are in threaded engagement via the second outer thread of the spindle 6 and the thread of the second splined portion 11 on the inside of the drive sleeve 10) are relaxed and allowed to return in their standby position. By returning of the spindle 6, the plug 8 within the drug containing cartridge 4 is allowed to relax towards the distal end of the drug delivery device.

Second Embodiment

Figure 2:
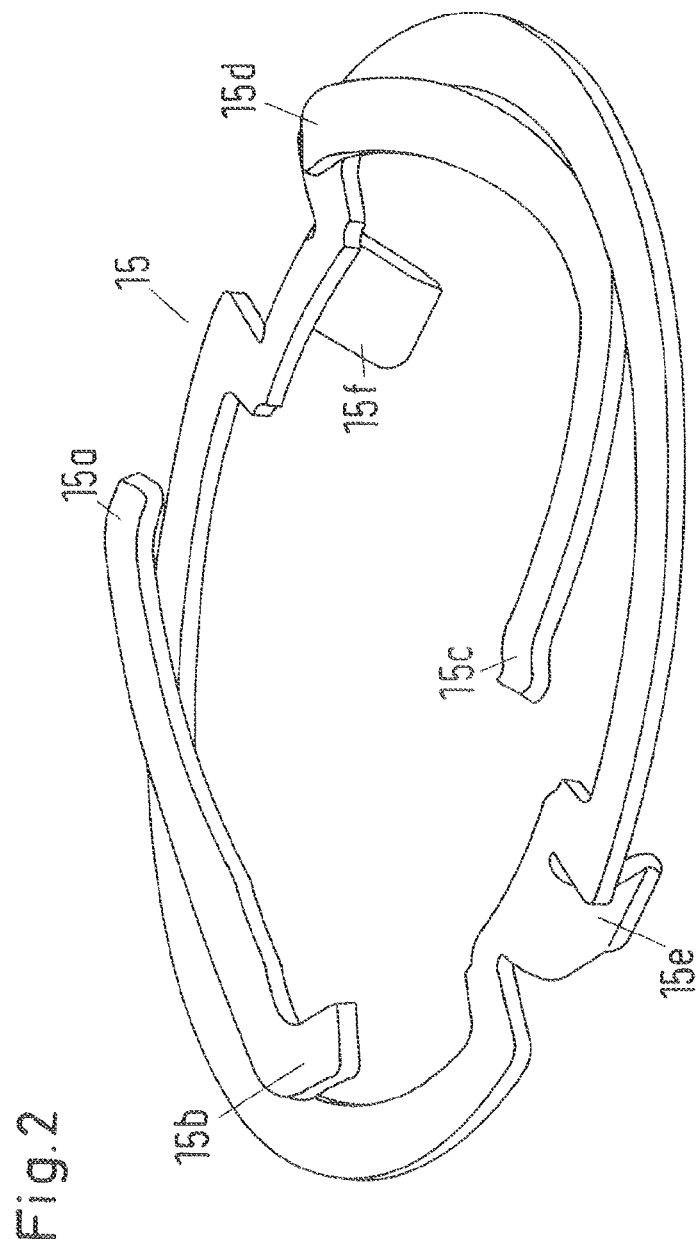
FIG. 2 shows a schematic drawing of the retraction means being designed as a spring element according to a second embodiment of the invention.
Figure 3:
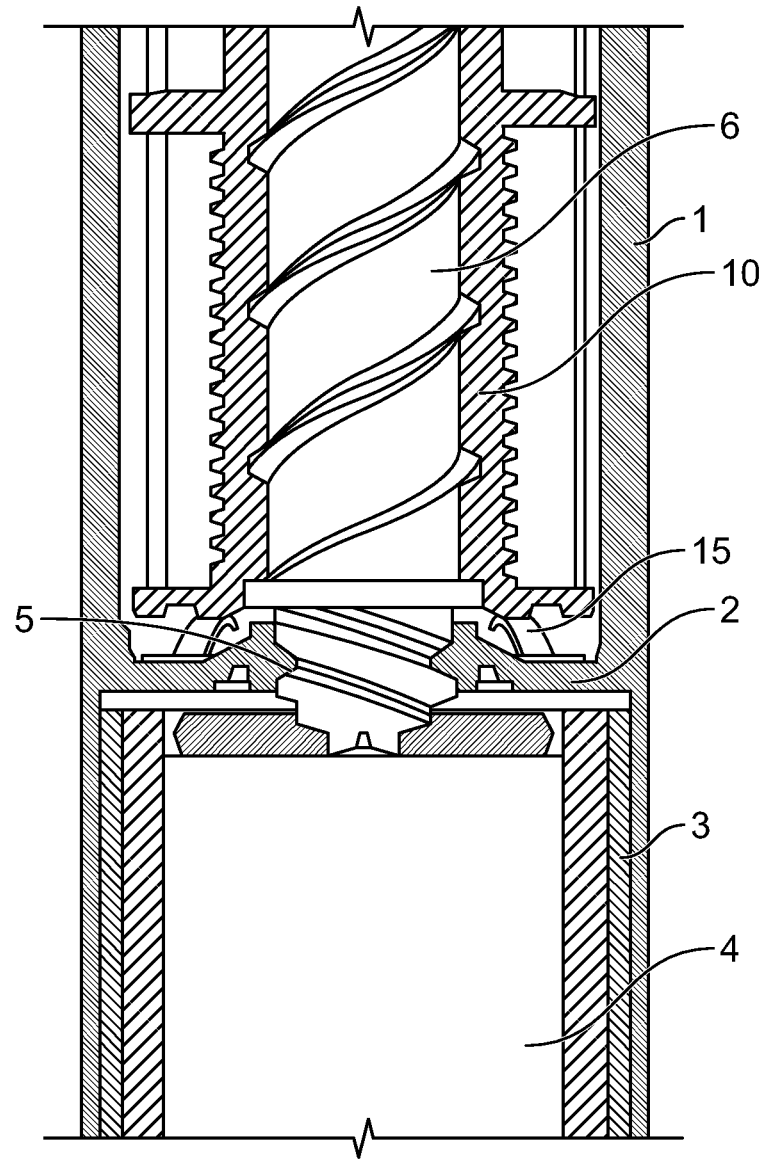
FIG. 3 shows a schematic sectional view of the drive mechanism with the spring element of FIG. 2.

According to the second embodiment, the retraction means is designed as a spring element 15 of the kind shown in FIG. 2. This spring element 15 is designed as a ring having flexible arms 15a, 15b, 15c, 15d which extend in the distal direction. Further arms 15e, 15f extend in the proximal direction for attachment of the spring element within the housing. The spring element 15 is borne in the bottom portion 2 or the inner wall of the housing 1. Preferably, it may be fixed by one or more clamps directed to the proximal end of the housing 1. The spring element 15 according to the second embodiment is applied between a proximal face of the drive sleeve 10 and the housing 1, in particular a bottom portion 2 or an inner wall of the housing 1, preferably an integrally moulded housing 1 (cf. FIG. 3). In this second embodiment, the drive sleeve 10 is in engagement with the spindle 6 via a second splined portion 11 provided on the drive sleeve.

The spring element 15 acts to displace the drive sleeve 10 within its dimensional tolerance (of the second splined portion 11) with respect to the housing 1 towards the distal end, so as to relieve stresses from the system at least at the end of the delivery step. Thereby, the plug 8 within the drug containing cartridge 4 is also allowed to relax after the delivery step towards the distal end of the drug delivery device.

Third Embodiment

Figure 4:
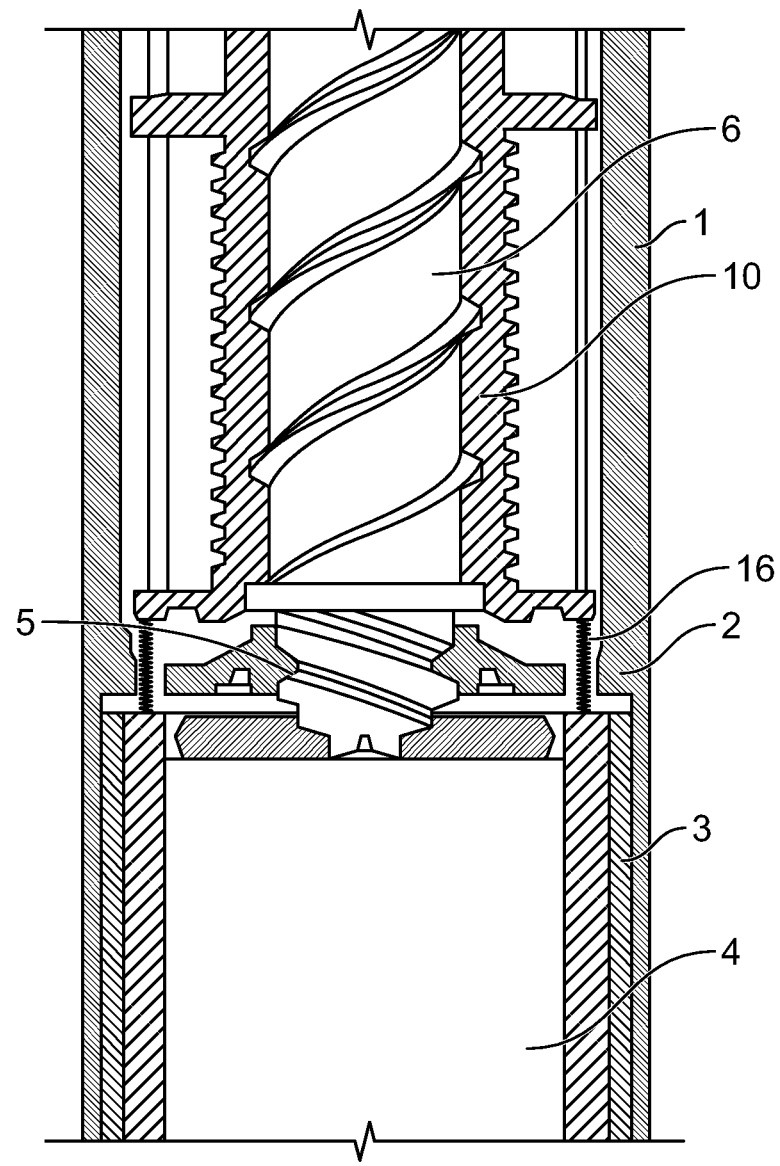
FIG. 4 shows a schematic sectional view of the drive mechanism according to a third embodiment in the standby position.
Figure 5:
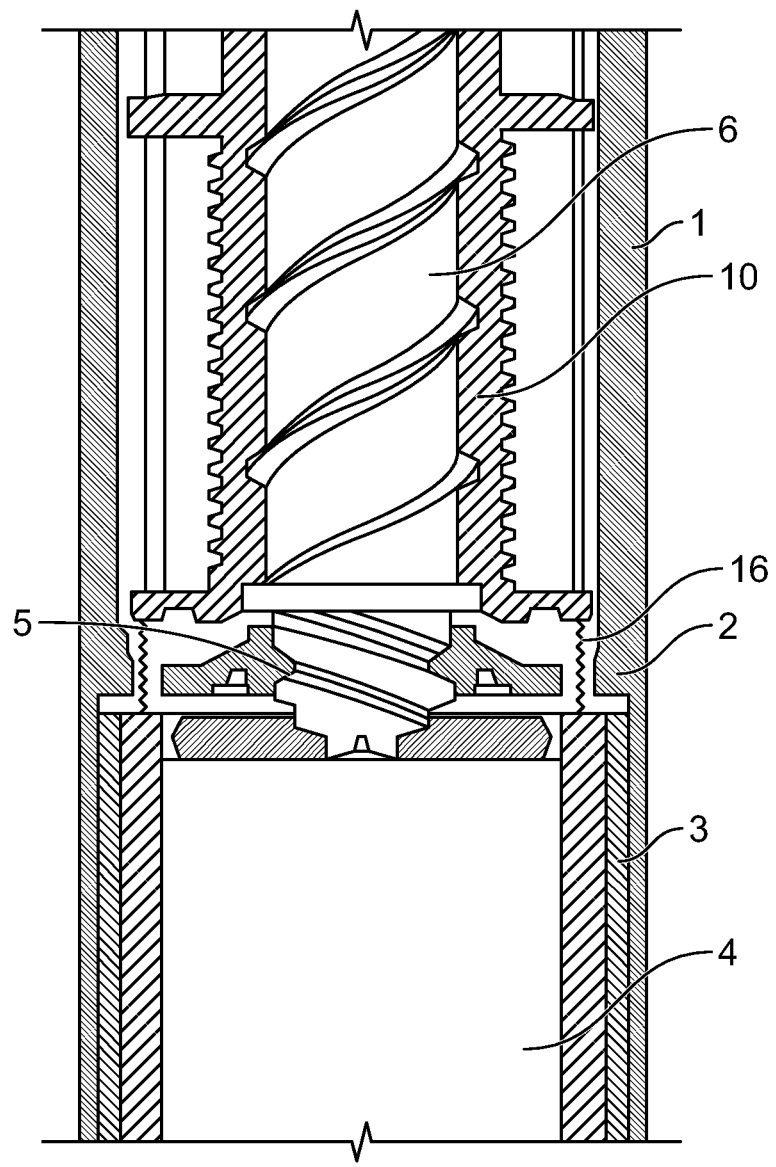
FIG. 5 shows a schematic sectional view of the drive mechanism according to a third particular embodiment while dispensing the drug to be delivered.

As a variation of the aforementioned second embodiment, a double spring element 16 of the kind shown in FIGS. 4 and 5 is applied in the third embodiment. This double spring element 16 is arranged between the drive sleeve 10 (having the second splined portion 11) and the drug containing cartridge 4. Preferably, it braces on one side on the drive sleeve 10 and on the other side on the drug containing cartridge 4, while the double spring element 16 is passed through the bottom portion 2 or the inner wall of the housing 1 by respective openings and may be fixed therein.

By this arrangement, stresses in the standby position of the drug delivery device are neutralised. The plug 8 within the drug containing cartridge 4 is allowed to relax into the distal direction, resulting in the above-mentioned advantages.

Moreover, in this arrangement the drug containing cartridge 4 is fixed in the axial direction by the spring force of the double spring element 16. This fixing is important as the mounting of an injection needle on the proximal end of the drug delivery device may displace the drug containing cartridge 4. A fixed drug containing cartridge 4 therefore also contributes to the reduction of dropping of the drugs to be delivered as well as improves the dose precision of the drugs to be delivered.

Another effect can be observed in the third embodiment. Since the double spring element 16 braces on one side on the drive sleeve 10 and on the other side on the drug containing cartridge 4, it is de-coupled from the bottom portion 2 of the housing 1. Hence, the bottom portion 2 is not deformed.

In the standby position (cf. FIG. 4) the housing 1 is relieved from stresses, but the double spring element 16 is braced between the first splined portion 5 and the drug containing cartridge 4. Therefore, no dropping is caused.

While dispensing the drug to be delivered (cf. FIG. 5), the double spring element 16 is mainly braced between the bottom portion 2 and the drug containing cartridge 4, which damps the oscillatory excitation of the bottom portion 2.

Accordingly, the advantages of the present invention are attained, namely reducing the stresses in the drug delivery device resulting in a reduction of dropping of the drugs to be delivered and a reduction of the dwell time.

As a further alternative, the spring element may be arranged between the drive sleeve 10 and the cartridge holder 3.

Forth Embodiment

Figure 6:
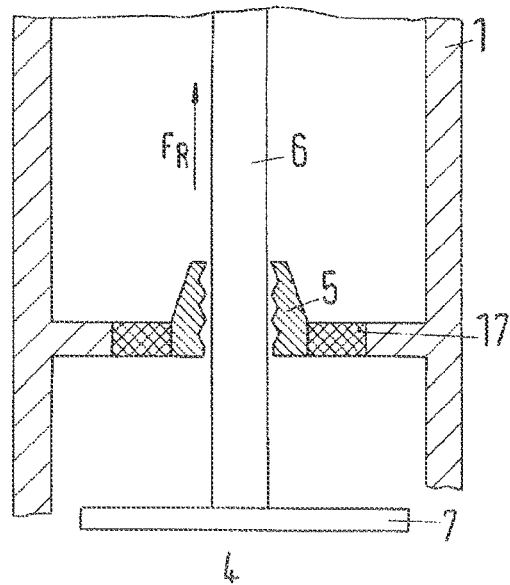
FIG. 6 shows a schematic sectional view of the drive mechanism according to a forth embodiment.

According to the forth embodiment, the retraction means may also be designed as a rubber element 17 cushioning a first splined portion 5 or socket engaging with the spindle 6 against the housing 1. This arrangement is shown in FIG. 6, wherein the housing 1 is provided with an inner wall extending in a radially inwards direction. The inner edge of the wall is provided with the first splined portion 5 or socket. A rubber element 17 or the like deformable element is provided between the housing 1 and the first splined portion 5 or socket, i.e. within the inner wall.

Similar to the above-mentioned embodiments, while operating the drive mechanism of the present invention the spindle 6 driving the plug 8 is moved towards the proximal end of the drug delivery device. At least at the end of the delivery step, the first splined portion 5 or socket engaging with the spindle 6 is axially displaced in the proximal direction by the flexibility of the rubber element 17.

After having ended the delivery operation, the axially displaced first splined portion 5 or socket via the rubber element 17 exerts a restoring force in the opposite direction of the movement of the spindle 6, whereby the spindle 6 and the drive sleeve 10 are relaxed and allowed to return in their standby position. By this returning of the spindle 6, the plug 8 within the drug containing cartridge 4 is allowed to relax towards the distal end of the drug delivery device.

The rubber element 17 may be of any material suitable for use in a drug delivery device and known to the person skilled in the art.

Fifth Embodiment

Figure 7:
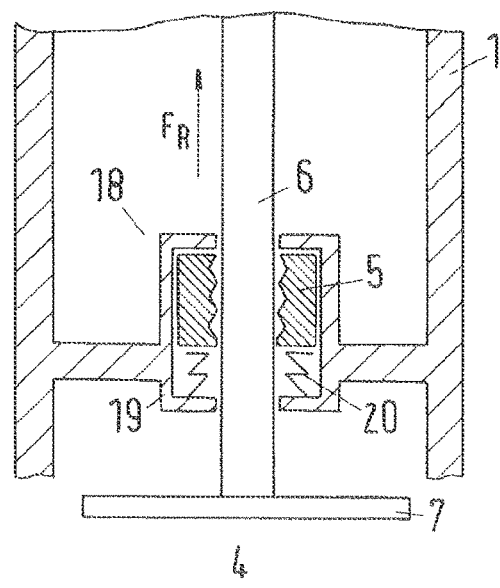
FIG. 7 shows a schematic sectional view of the drive mechanism according to a fifth embodiment.

According to the fifth embodiment, a bearing element 18 builds up the retraction means, as shown in FIG. 7. The housing 1 is provided with an inner wall extending in a radially inwards direction. Therein embedded is an element frame 19, in which a spring element 20 cushions a first splined portion 5 or socket engaging with the spindle 6 against the bearing element Similar to the above-mentioned forth embodiment, the spindle 6 driving the plug 8 is moved towards the proximal end of the drug delivery device, while the drive mechanism of the present invention is operated. At least at the end of the delivery step, the first splined portion 5 or socket engaging with the spindle 6 is axially displaced in the proximal direction by the spring force of the spring element.

After having ended the delivery operation, the axially displaced first splined portion 5 or socket via the spring element 20 exerts a restoring force in the opposite direction of the movement of the spindle 6, whereby the spindle 6 and the drive sleeve 10 are relaxed and allowed to return in their standby position. By this returning of the spindle 6, the plug 8 within the drug containing cartridge 4 is allowed to relax towards the distal end of the drug delivery device.

Sixth Embodiment

In addition to the above embodiments or as an alternative thereto, the plug 8 acting within the drug containing cartridge 4 can be designed so as to reduce the actuating force of the whole drug delivery device.

Figure 8:
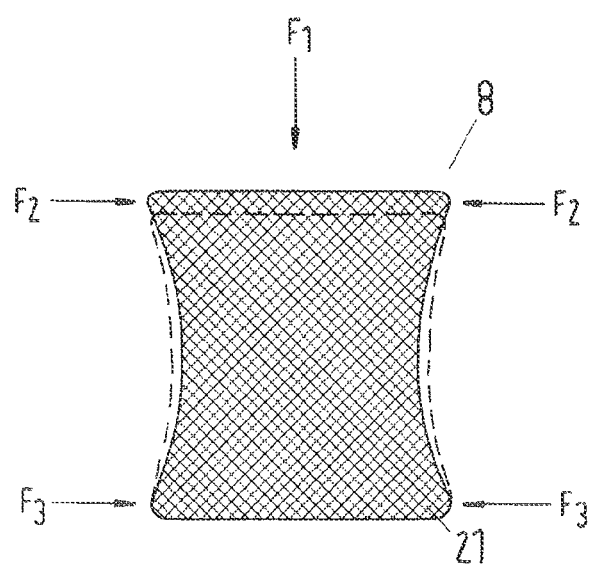
FIG. 8 shows a schematic drawing of a conventional plug according to the state of the art, which is loaded with an actuating force F1.

When a conventional plug 8 according to the state of the art is loaded with an actuating force F1 (dispensing force of the drug to be delivered), the elasticity of the plug 8 results in an increase of the forces F2 and F3 at the sealing lips 21, which is schematically shown in FIG. 8. The plug 8 itself is compressed. Because of this, the friction force between the sealing lips 21 and the wall of the drug containing cartridge 4 is increased. Therefore, the force required to move the plug 8 is also increased.

After having ended the drug delivery step, the conventional plug 8 cannot relax towards the distal end of the drug delivery device, it can only relieve its stress in the proximal direction, resulting in dropping of the drug to be delivered and longer dwell time.

Figure 9:
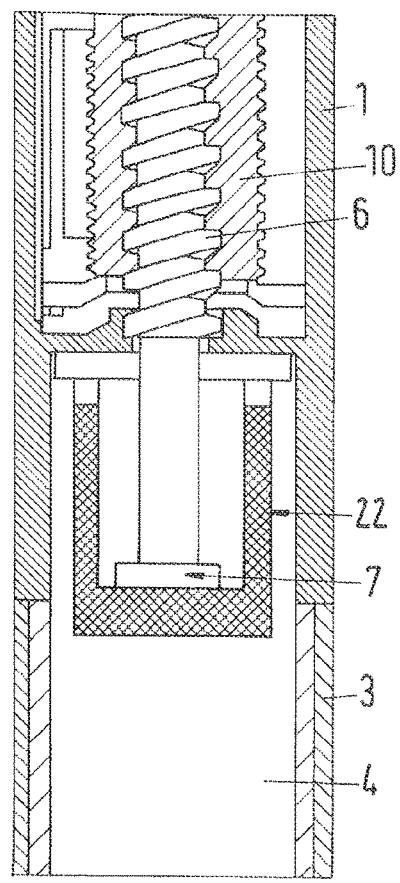
FIG. 9 shows a schematic sectional view of the drive mechanism according to a sixth embodiment.
Figure 10:
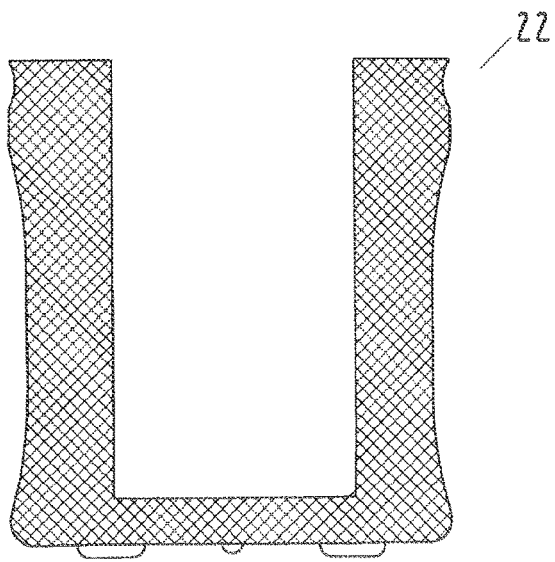
FIG. 10 shows an engineering drawing of the hollow plug according to a sixth embodiment.

To overcome this drawbacks, a hollow plug 22 according to this embodiment is provided, which has a cup-shape and is of flexible material (cf. FIG. 9). The hollow plug 22 is abutted by the spindle 6 and acts in the drug containing cartridge 4. It has a wall thickness of at least 1 mm, a bottom thickness (adjacent to the drug contained in the cartridge 4) of at least 1 mm and a clearance between the centreline perpendicular to the axial direction and the inner bottom face of at least 1 mm. As an example, an engineering drawing of the hollow plug 22 dimensions is depicted in FIG. 10.

Figure 11:
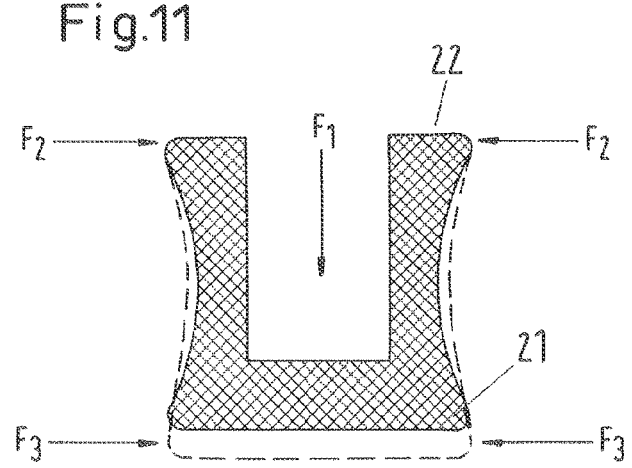
FIG. 11 shows a schematic drawing of the hollow plug according to a sixth embodiment.

In detail, the loading of the hollow plug 22 with the actuating force F1 is executed in the interior of the hollow plug 22, as can be seen in the schematic drawing of FIG. 11. By loading the actuating force to the hollow plug 22, the same is elongated. At that time, the force F2 is decreased, while the force F3 is increased or remains even unchanged, which results in lowering of the friction surface between the hollow plug 22 and the wall of the drug containing cartridge 4. Accordingly, the actuating force required for moving the hollow plug 22 is decreased.

After having ended the drug delivery step, the hollow plug 22 is allowed to return to its initial shape. The bottom face of the hollow plug 22 (contact face to the drug to be delivered) remains at its final position, while the wall portion of the hollow plug 22 contracts and thereby relieves the system from stresses.

Therefore, no additional force is loaded to the drug to be delivered so that dropping and increasing of dwell time are avoided.

The hollow plug 22 may be of any material suitable for use in a drug containing cartridge 4 and known to the person skilled in the art.

The invention claimed is:

1. A drive mechanism for a drug delivery device, preferably for a pen-type injector, said drive mechanism comprising:
    a spindle movable in a first direction during a delivery step of dispensing medicament in said drug delivery device,
    a splined portion operatively coupled to said spindle such that the spindle rotates relative to the splined portion during the delivery step,
    a retraction means configured as an elastic portion, wherein the retraction means is configured to exert, in a second direction contrary to the first direction, a restoring force on said splined portion at least at an end of said delivery step to cause said spindle and/or said splined portion to move axially in the second direction contrary to said first direction, and
    a cartridge holder for accommodating a cartridge containing a drug to be delivered,
    wherein the restoring force causes the spindle and/or the splined portion to move axially in the second direction without relative rotation between the spindle and the splined portion,
    wherein the splined portion is threadedly engaged with the spindle to allow the relative rotation therebetween, wherein a clearance exists between threads of the splined portion and respective threads of the spindle.

2. The drive mechanism according to claim 1, wherein the elastic portion is designed as a spring element.

3. The drive mechanism according to claim 1, wherein the elastic portion is designed as a rubber element cushioning a splined socket engaging with the spindle.

4. The drive mechanism according to claim 1 further comprising a housing, with said retraction means being arranged between said splined portion and said housing.

5. The drive mechanism according to claim 1, further including:
    a housing, wherein the retraction means is configured as a portion extending radially inward from an inner surface of the housing.

6. The drive mechanism according to claim 1, wherein the splined portion is designed as or a component of a driver acting on said spindle to move said spindle in the first direction during the delivery step.

7. The drive mechanism according to claim 1, wherein the splined portion is designed as a spindle nut rotationally fixed with respect to a housing of the drive mechanism.

8. The drive mechanism according to claim 1, wherein the spindle abuts to a hollow plug having a cup-shape and being of flexible material, said hollow plug acting in the cartridge containing the drug to be delivered.

9. The drive mechanism according to claim 8, wherein said hollow plug has a wall thickness of at least 1 mm, a bottom thickness of at least 1 mm and a clearance between the centerline perpendicular to an axial direction and an inner bottom face of at least 1 mm.

10. The drive mechanism according to claim 1,
wherein the spindle is designed as a threaded piston rod and the splined portion is designed as a nut-like element which is in engagement with the threaded piston rod,
wherein the threaded piston rod has a thread disposed on an outer peripheral surface of the threaded piston rod and engages with a respective thread disposed on an inner peripheral surface of the splined portion, and
wherein a pitch of the thread of the threaded piston rod and a pitch of the respective thread of the splined portion are chosen such that relative axial movement between the threaded piston rod and the nut-like element is allowed.

11. The drive mechanism according to claim 10, wherein the splined portion is a first splined portion, the thread of the threaded piston rod is a first thread, and the respective thread of the first splined portion is a first respective thread, the drive mechanism further comprising:
a drive sleeve having a second splined portion having a second respective thread disposed on an inner peripheral surface of the second splined portion, wherein the threaded piston rod has a second thread disposed on the outer peripheral surface of the threaded piston rod configured to engage with the second respective thread of the drive sleeve, and wherein the pitch of the first thread is different from a pitch of the second thread.

12. The drive mechanism according to claim 1, further comprising a dose knob, and wherein the end of said delivery step correspond to when a user releases the dose knob of the drive mechanism.

13. A drive mechanism for a drug delivery device, said drive mechanism comprising:
a spline moveable in a proximal direction during a delivery step of dispensing medicament in said drug delivery device,
a splined portion operatively coupled to a spindle such that the spindle rotates relative to the splined portion, and
a retraction element configured as an elastic portion, wherein the retraction element is configured to act on said splined portion at least at an end of said delivery step such that at the end of said delivery step at least one of said spindle or said splined portion is moved in a distal direction, to cause said at least one of said spindle or said splined portion to move towards the distal end of said drug delivery device,
wherein the spindle is designed as a threaded piston rod and the splined portion is designed as a nut-like element which is in engagement with the threaded piston rod,
wherein the threaded piston rod has a thread disposed on an outer peripheral surface of the threaded piston rod and engages with a respective thread disposed on an inner peripheral surface of the splined portion, and
wherein a pitch of the thread of the threaded piston rod and a pitch of the respective thread of the splined portion are chosen such that relative axial movement between the threaded piston rod and the nut-like element is allowed,
wherein the splined portion is a first splined portion, the thread of the threaded piston rod is a first thread, and the respective thread of the first splined portion is a first respective thread, the drive mechanism further comprising:
a drive sleeve having a second splined portion having a second respective thread disposed on an inner peripheral surface of the second splined portion, wherein the threaded piston rod has a second thread disposed on the outer peripheral surface of the threaded piston rod configured to engage with the second respective thread of the drive sleeve, and wherein the pitch of the first thread is different from a pitch of the second thread.

14. The drive mechanism of claim 13, further comprising a dose knob, and wherein the end of said delivery step corresponds to when a user releases the dose knob of the drive mechanism.

* * * * *